United States Patent [19]

Kumobayashi et al.

[11] Patent Number: 4,604,474
[45] Date of Patent: Aug. 5, 1986

[54] RHODIUM-PHOSPHINE COMPLEX

[75] Inventors: Hidenori Kumobayashi; Susumu Akutagawa, both of Kanagawa, Japan

[73] Assignee: Takasago Perfumery Co., Ltd., Tokyo, Japan

[21] Appl. No.: 714,281

[22] Filed: Mar. 21, 1985

[30] Foreign Application Priority Data

Mar. 22, 1984 [JP] Japan .................................. 59-53600

[51] Int. Cl.⁴ .............................................. C07F 15/00
[52] U.S. Cl. ......................................... 556/7; 556/16; 556/22; 556/23
[58] Field of Search ........................ 556/7, 22, 23, 16

[56] References Cited

U.S. PATENT DOCUMENTS

| | | | |
|---|---|---|---|
| 3,798,241 | 3/1974 | Kagan et al. | 556/22 X |
| 3,949,000 | 4/1976 | Violet | 556/23 X |
| 4,142,992 | 3/1979 | Knowles et al. | 556/7 X |
| 4,166,824 | 9/1979 | Henderson, Jr. | 556/22 |
| 4,187,241 | 2/1980 | Townsend et al. | 556/23 |
| 4,201,728 | 5/1980 | Hughes | 556/16 X |
| 4,356,324 | 10/1982 | Bergstein et al. | 556/7 X |
| 4,393,240 | 7/1983 | Stille | 556/7 X |
| 4,397,787 | 8/1983 | Riley | 556/7 X |
| 4,451,450 | 5/1984 | Subramanyam | 556/22 X |

OTHER PUBLICATIONS

JACS 106, pp. 5208–5217 (1985).
Angew. Chem. Int. Ed. Eng. 24, No. 3, pp. 217 to 219 (1985).

Primary Examiner—Helen M. S. Sneed
Attorney, Agent, or Firm—Sughrue, Mion, Zinn, Macpeak, and Seas

[57] ABSTRACT

A novel rhodium-phosphine complex represented by the formula $$[Rh(p\text{-}Tolyl\ BINAP)_2]^+Y^-$$

wherein p-Tolyl BINAP represents 2,2'-bis(di-p-tolyl-phosphino)-1,1'-binaphthyl, and Y represents ClO₄, PF₆, BF₄ or PCl₆ is described. This complex can be used as a catalyst for various organic syntheses and also for asymmetric syntheses such as an asymmetric isomerization reaction and an asymmetric hydrogenation reaction. Due to its high activity, the complex is very useful as a catalyst.

1 Claim, 1 Drawing Figure

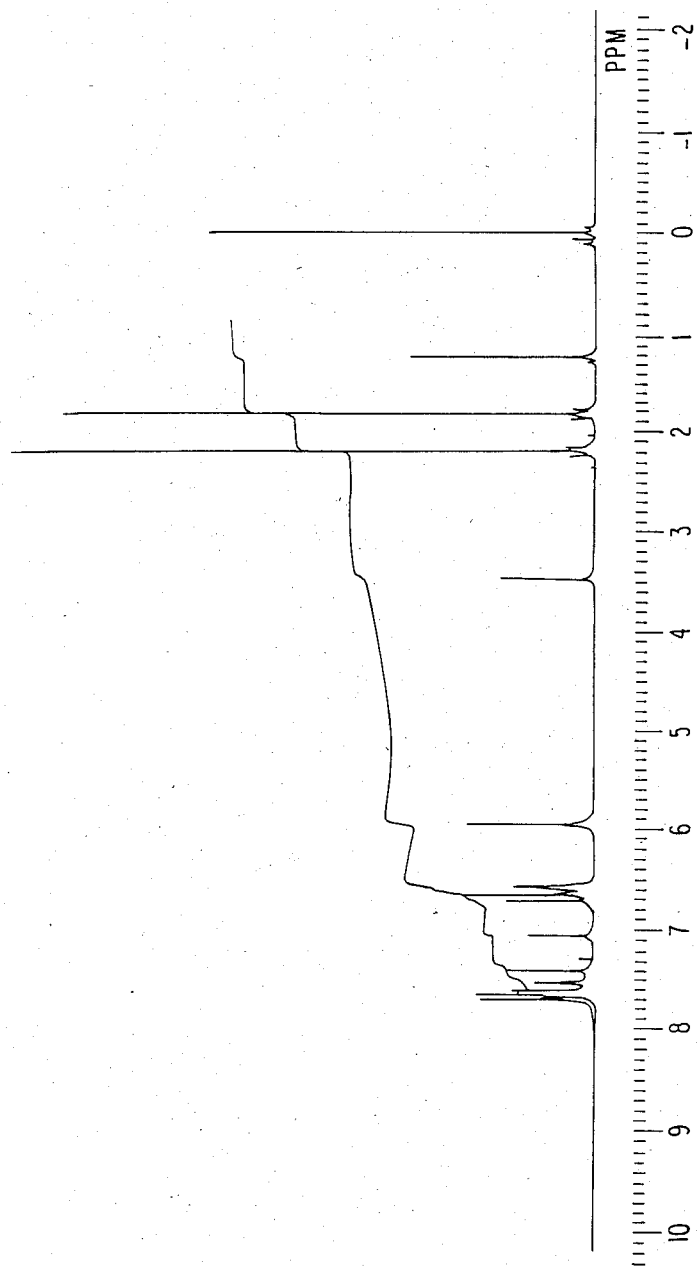

RHODIUM-PHOSPHINE COMPLEX

FIELD OF THE INVENTION

The present invention relates to a rhodium-phosphine complex. More particularly, it is concerned with a rhodium-phosphine complex which is used as an industrial catalyst in preparation of chiral compounds from prochiral compounds by various organic syntheses and asymmetric syntheses such as an asymmetric isomerization reaction and an asymmetric hydrogenation reaction.

BACKGROUND OF THE INVENTION

Many transition metal complexes have heretofore been used as catalysts for preparation of organic compounds. In particular, noble metal complexes are stable and are easy to handle although those are expensive. Thus, extensive investigations are made on syntheses utilizing such noble metal complexes as catalysts. In particular, many reports are issued with respect to asymmetric catalysts used in asymmetric syntheses such as asymmetric isomerization reaction and asymmetric hydrogenation reaction.

In general, rhodium, palladium and nickel catalysts with tert-phosphine as an optically active ligand provided thereto give good results. Japanese Patent Application (OPI) No. 61937/80, for example, discloses a rhodium/phosphine catalyst as an asymmetric hydrogenation catalyst, in which chiral phosphine is coordinated to rhodium. The term "OPI" as used herein means a "published unexamined Japanese patent application".

Japanese Patent Application (OPI) No. 4748/83 discloses an asymmetric hydrogenation catalyst and also discloses a method of preparing enamines or imines by isomerization of allylamine derivatives using as an asymmetric isomerization catalyst a rhodium complex represented by the formula (II):

$$[Rh(olefin)L]^+X^- \quad (II)$$

wherein the olefin represents ethylene, 1,3-butadiene, norbornadiene or cycloocta-1,5-diene; X represents $ClO_4$, $BF_4$ or $PF_6$; and L represents two triarylphosphines or a trivalent phosphine compound represented by the formula (III):

(III)

wherein Z is

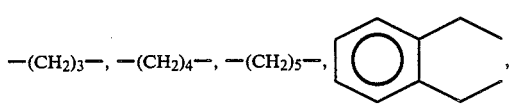

For example, neryldiethylamine is subjected to isomerization and the enamine thus prepared is hydrolyzed to obtain optically active citronellal.

These catalysts, however, have various disadvantages. One of the disadvantages is that their production costs are high since they are prepared using expensive metals and their preparation steps are complicated. This results in increasing the price of the desired compound. Another disadvantage is that although their catalytic activity is high, such a high activity cannot be maintained for long periods of time, or conversely, although their catalytic life or durability is long, activity is relatively low. Thus, they are not suitable for use in industrial applications.

As a catalyst which can overcome the above-described disadvantages, Japanese Patent Application (OPI) No. 169283/83 (corresponding U.S. patent application Ser. No. 651,123, filed Sept. 17, 1984) discloses a rhodium-phosphine complex represented by the formula (IV)

$$[Rh(BINAP)_2]^+Q^- \quad (IV)$$

wherein BINAP represents 2,2'-bis(diphenylphosphino)-1,1'-binaphthyl, and Q represents $ClO_4$, $PF_6$, $BF_4$, $PCl_6$ or $B(C_6H_5)_4$. However, this catalyst is not completely satisfactory in industrial uses.

Under such circumstances, it has been desired to develop catalysts which are inexpensive, have a high activity and can maintain such a high activity for long periods of time.

SUMMARY OF THE INVENTION

As a result of investigations to meet such industrial demands, the present inventors have found a novel complex catalyst having a high activity which can be used as a catalyst for general syntheses by using ligands having no optical activity therein and which can be used as a catalyst for asymmetric syntheses by using ligands having an optical activity, and established the synthesis method.

Accordingly, the object of the present invention is to provide a novel rhodium-phosphine complex which can be used as a catalyst for various organic syntheses and also for asymmetric syntheses and, furthermore, which has a high activity and can maintain such a high activity for long periods of time.

A novel rhodium-phosphine complex useful as a catalyst according to the present invention is represented by the formula (I):

$$[Rh(p\text{-Tolyl BINAP})_2]^+Y^-$$

wherein p-Tolyl BINAP represents 2,2'-bis(di-p-tolylphosphino)-1,1'-binaphthyl; and Y represents $ClO_4$, $PF_6$, $PF_4$ or $PCl_6$.

BRIEF DESCRIPTION OF THE DRAWING

The FIGURE is an NMR spectrum of [Rh(−)p-Tolyl BINAP)$_2$]$^+$ ClO$_4^-$ obtained in Example 1 of the present invention.

DETAILED DESCRIPTION OF THE INVENTION

The rhodium-phosphine complex of the present invention can be prepared in high yields by reacting a rhodium complex represented by the formula (V):

[Rh(olefin) (p-Tolyl BINAP)]$^+$Y$^-$  (V)

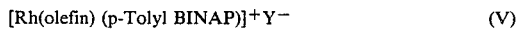

wherein the olefin represents ethylene 1,3-butadiene, cyclohexadiene, norbornadiene or cycloocta-1,5-diene; p-Tolyl BINAP represents 2,2′-bis(di-p-tolylphosphino)-1,1′-binaphthyl which is a racemic substance or optically active substance; and Y represents ClO$_4$, PF$_6$, BF$_4$ or PCl$_6$, with one molecule of p-Tolyl BINAP in a soluble solvent such as tetrahydrofuran or acetone.

In one embodiment of the present invention, a rhodium complex of the formula (V) is dissolved in a suitable soluble solvent, an equimolar or excess amount of p-Tolyl BINAP is added thereto, and the resulting homogeneous solution is then hydrogenated in an atmospheric pressure hydrogenating apparatus. This hydrogenation is carried out at a temperature of from 10° to 50° C. The time required for the hydrogenation process is from 1 to 10 hours. The reaction is determined to be completed when hydrogen absorption finishes. In the case that the pressure of hydrogen is (sub)stmospheric pressure, the reaction is completed when hydrogen in the number of moles equal to that of rhodium is absorbed. In the case that the pressure of hydrogen is, for example, about 5 Kg/cm$^2$, the reaction is sometimes completed by absorbing 2 moles per mole of rhodium of hydrogen.

The solvent is then distilled away from the reaction mixture, thereby obtaining the novel complex of the formula (I) of the present invention in a crystal form. Industrially the reaction mixtures can be directly used, i.e., without distilling away the solvent. Solvents which can be used include tetrahydrofuran, acetone and dichloromethane.

In another embodiment, the novel complex of the present invention can be prepared as follows:

A rhodium complex of the formula (V) is dissolved in a soluble solvent such as tetrahydrofuran or acetone, and an equimolar or excess amount of p-Tolyl BINAP to the rhodium complex is added thereto. The resulting mixture is heated to 50° to 60° C. After the reaction is completed, the solvent is distilled away. A fresh solvent is again added to prepare a homogeneous solution, and then the same reaction as above is repeated. The solvent is distilled away under reduced pressure. This operation is repeated two to four times, thereby obtaining the complex of the formula (I).

A racemic substance and/or an optically active substance of p-Tolyl BINAP required to prepare the complex (I) of the present invention can be prepared by the following method:

Bromine is reacted with 1,1′-bi-2-naphthol using triphenylphosphine as a reaction aid to prepare 2,2′-dibromo-1,1′-binaphthyl. The resulting product is subjected to the preparation method of the conventional Grignard reagent, e.g., using magnesium, to prepare Grignard reagent. The resulting reagent is condensed with di-p-tolylphosphinylchloride to obtain (±)-2,2′bis(di-p-tolylphosphinyl)-1,1′-binaphthyl. The resulting product is heated together with trichlorosilane to reduce, thereby obtaining (±)-2,2′-bis(di-p-tolylphosphino)-1,1′-binaphthyl((±)p-Tolyl BINAP).

In the case of obtaining p-Tolyl BINAP which is an optically active substance, the method disclosed in Henri Brunner, Angw. Chem. Int. Edt. Engl. 18, 620 (1979) is employed. That is, (±)-2,2′-bis(di-p-tolylphosphinyl)-1,1′-binaphthyl is resolved using dibenzoyl tartrate to separate an optically active substance, and the resulting product is reduced with trichlorosilane to obtain optically active o-Tolyl BINAP. If desired and necessary, only one optically active substance can be selectively obtained by selecting d-form or l-form of dibenzoyl tartrate as a resolving agent.

The rhodium complex of the formula (V) can be easily prepared by reacting rhodium trichloride with an olefin such as cycloocta-1,5-diene in a solvent such as methanol or ethanol to prepare a rhodium/olefin complex, and then reacting the rhodium/olefin complex with p-Tolyl BINAP which is a racemic substrate or optically active substance as a trivalent phosphine compound.

The rhodium-phosphine complex of the present invention can be used as a catalyst for various organic syntheses and also for asymmetric syntheses such as an asymmetric isomerization reaction and an asymmetric hydrogenation reaction.

The rhodium-phosphine complex of the present invention has a high activity. That is, the activity of the rhodium-phophine complex of the present invention is about 1.2 to 1.4 times that of conventionally used catalyst such as [Rh(BINP)$_2$]$^+$ ClO$_4^-$ or [Rh(BINAP)$_2$]$^+$ PF$_6^-$. This contributes greatly to a reduction in production costs. The rhodium-phosphine complex similarly prepared using an optically active ligand is useful as a catalyst in asymmetric syntheses.

This effect is explained in the case of applying to the isomerization reaction of allylamine.

Allylamine can be isomerized using as a catalyst the rhodium-phosphine complex of the present invention, the molar ratio of allylamine to the complex being 6000:1 to 8000:1. In the subsequent reactions it is sufficient for the rhodium-phosphine complex to be supplemented in an amount of 7 to 8% by weight based on the weight of the catalyst added in the first reaction. By repeating this procedure, the allylamine in the amount of about 130,000 times that of the rhodium-phosphine complex could be isomerized into enamine. The optical purity of the product obtained is sufficiently satisfactorily high.

The present invention is described in greater detail by reference to the following examples and application examples.

EXAMPLE 1

14.8 g of [Rh(cycoocta-1,5-diene) ((−)-p-Tolyl BINAP)]$^+$ClO$_4^-$ was suspended in 750 ml of tetrahydrofuran, and 10.17 g of (−)-p-Tolyl BINAP (mp: 257°-258° C., [α]$_D^{25}$: −169.49° ($c$=1.052, benzene) was added thereto to prepare a homogeneous solution. This homogeneous solutin was placed in an atmospheric pressure hydrogenating apparatus, and hydrogenation was carried out at 25° to 30° C. After about 13 hours, absorption of hydrogen was not observed. At this point, the reaction was determined to be completed. The tetrahydrofuran used as a solvent was distilled away under reduced pressure to obtain 23.4 g of reddish brown crystals of the desired [Rh((−)-p-Tolyl BINAP)₂]⁺·ClO₄⁻.

The elemental analysis values of the complex thus obtained are as follows:

|  | C | H | P | Cl | Rh |
|---|---|---|---|---|---|
| Found | 73.52 | 5.35 | 8.10 | 2.05 | 6.43 |
| Calculated | 73.92 | 5.13 | 7.96 | 2.28 | 6.60 |

The values of proton NMR in the p-Tolyl BINAP portion of the complex [Rh((−)-p-Tolyl BINAP)₂]⁺·ClO₄⁻ are as follows:

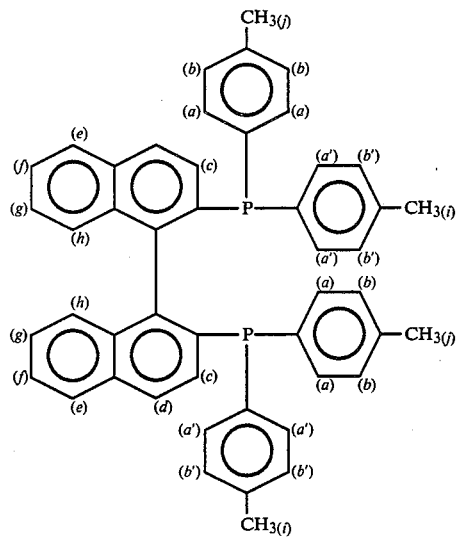

NMR (δ ppm): (a) 5.95 (4H,d), (b) 6.6 (4H,d), (c) 7.70 (2H,d), (d) 7.5 (2H,d), (e) 7.65 (2H,d) (f) 7.38 (2H,t), (g) 7.05 (2H,t), (h) 6.72 (2H,d), (a') 6.65 (4H,d), (b') 7.61 (4H,d), (i) 1.80 (6H,s) (j) 2.17 (6H,s).

The NMR spectrum was measured using J.N.M-GX-400 Model apparatus (400 MHZ), manufactured by JEOL LTD.

The spectrum obtained is shown in the accompanying drawing.

EXAMPLE 2

15.09 g of [Rh(cyclohexa-1,3-diene)((+)-p-Tolyl BINAP)]⁺ PF₆⁻ was suspended in 750 ml of acetone, and 10.17 g of (+)-p-Tolyl BINAP (mp: 257°–258° C., [α]$_D^{25}$: +174.04° (C=0.886, benzene)) was added thereto to prepare a homogeneous solution. This homogeneous solution was placed in an atmospheric pressure hydrogenating apparatus, and hydrogenation was carried out at 25° to 30° C. After about 15 hours, absorption of hydrogen was not observed. At this point, the reaction was determined to be completed. The acetone used as a solvent was distilled away under reduced pressure to obtain 24 g of brown crystals of the desired [Rh((+)-p-Tolyl BINAP)₂]⁺ PF₆⁻.

The elemental analysis values of the complex thus obtained are as follows.

|  | C | H | P | F | Rh |
|---|---|---|---|---|---|
| Found | 72.11 | 5.03 | 9.82 | 6.98 | 6.27 |
| Calculated | 71.82 | 4.98 | 9.66 | 7.10 | 6.42 |

EXAMPLE 3

9.6 g of [Rh(norbornadiene)((+)-p-Tolyl BINAP)]⁺ BF₄⁻ and 6.78 g of (+)-p-Tolyl BINAP were hydrogenated in tetrahydrofuran in the same manner as in Example 1 to obtain 15.47 g of brown crystals of [Rh(+)-p-Tolyl BINAP)₂]⁺ BF₄⁻.

The elemental analysis values of the complex thus obtained are as follows.

|  | C | H | P | F | Rh |
|---|---|---|---|---|---|
| Found | 74.81 | 5.34 | 8.13 | 4.71 | 6.35 |
| Calculated | 74.53 | 5.18 | 8.02 | 4.92 | 6.66 |

EXAMPLE 4

11.3 g of [Rh(cycloocta-1,5-diene)((−)-p-Tolyl BINAP)]⁺ PCl₆⁻ and 6.78 g of (−)-p-Tolyl BINAP were hydrogenated in acetone in the same manner as in Example 1 to obtain 17.13 g of reddish brown crystals of [Rh((−)-p-Tolyl BINAP)₂]⁺ PCl₆⁻.

The elemental analysis values of the complex thus obtained are as follows.

|  | C | H | P | Cl | Rh |
|---|---|---|---|---|---|
| Found | 67.81 | 4.93 | 5.97 | 8.98 | 12.14 |
| Calculated | 67.66 | 4.70 | 6.04 | 9.02 | 12.51 |

EXAMPLE 5

14.8 g of [Rh(cycloocta-1,5-diene)((±)-p-Tolyl BINAP)]+ClO₄⁻ was suspended in 740 ml of tetrahydrofuran, and 10.17 g of (±)-p-Tolyl BINAP was added therto to prepare a homogeneous solution. This homogeneous solution was placed in an atmospheric pressure hydrogenating apparatus, and hydrogenation was carried out at 30° C. After 15 hours, absorption of hydrogen was not observed. At this point, the reaction was determined to be completed. The tetrahydrofuran used as a solvent was distilled away under reduced pressure to obtain 23.5 g of reddish brown crystals of the desired [Rh(+)-p-Tolyl BINAP)₂]+ClO₄⁻.

The elemental analysis values of the complex thus obtained are as follows:

|  | C | H | P | Cl | Rh |
|---|---|---|---|---|---|
| Found | 72.68 | 5.48 | 7.54 | 2.13 | 6.85 |
| Calculated | 73.92 | 5.13 | 7.96 | 2.28 | 6.60 |

APPLICATION EXAMPLE 1

The air in a 1 liter pressure vessel was replaced by nitrogen. Under a nitrogen atmosphere, 10 ml (0.2 millimole) of a tetrahydrofuran solution of the complex [Rh((−)-p-Tolyl BINAP)₂]+ClO₄⁻ prepared in Example 1, 200 ml of tetrahydrofuran and 334 g of N,N-diethylgeranylamine were placed in the vessel and reacted at 100° C. for 15 hours. After the reaction was completed, the reaction mixture was transferred into a distillation column. After the tetrahydrofuran was distilled away, the resulting residue was further distilled under reduced pressure to obtain 330 g of the isomerized product, citronellaldiethylenamine (purity, 99%).

To the distillation residue was added 10 ml of n-heptane. The mixture was sufficiently stirred to dissolve high boiling components and by-product components in n-heptane and a n-heptane soluble portion was removed by filtration. 10 ml of fresh n-heptane was added and the same procedure as above was repeated. Thereafter, 200 ml of tetrahydrofuran was added to the distillation column and the remaining catalyst was dissolved therein to prepare a homogeneous solution. This homogeneous solution was returned to the 1 liter pressure vessel. 0.7 ml (0.014 millimole) of a fresh catalyst solution was added, and 334 g of N,N-diethylgeranylamine was added. The second reaction was carried out, whereby citronellaldiethylenamine of the same purity as in the first reaction was obtained in nearly the same amount as in the first reaction.

Thereafter, the same procedure as above was repeated 25 times and the same results could be obtained.

Citronellaldiethylenamine thus obtained was dissolved in the same amount of toluene. 0.55 mole per mole of the enamine of 10% sulfuric acid was added to the resulting mixture at 0° to 5° C. to hydrolyze, followed by treating in the conventional manners. The resulting hydrolyzate was distilled under a reduced pressure to obtain d-citronellal having a purity of 99.8%.

The optical rotation, $[\alpha]_D^{25}$, of the product was $+16.37°$, and in view of the literature value $[\alpha]_D = +16.5°$, the optical purity was 99.7%.

APPLICATION EXAMPLE 2

The air in a 1 liter pressure vessel was replaced by nitrogen. Under a nitrogen atmosphere, 20 ml (0.2 millimole) of a tetrahydrofuran solution of the complex $[Rh((+)-p-Tolyl\ BINAP)_2]^+PF_6^-$ prepared in Example 2, 200 ml of tetrahydrofuran and 251 g (1.2 moles) of N,N-diethylnerylamine were placed in the vessel and reacted at 110° C. for 15 hours. After the reaction was completed, the reaction mixture was transferred into a distillation column. After the tetrahydrofuran was distilled away, the resulting residue was further distilled under reduced pressure to obtain 249 g of the isomerized product, citronellaldiethylenamine (purity, 98.3%).

To the distillation residue was added 10 ml of n-heptane. The mixture was sufficiently stirred to dissolve high boiling components and by-product components in n-heptane and a n-heptane soluble portion was removed by filtration. 10 ml of fresh n-heptane was added and the same procedure as above was repeated. Thereafter, 200 ml of tetrahydrofuran was added to the distillation column and the remaining catalyst was dissolved therein to prepare a homogeneous solution. This homogeneous solution was returned to the 1 liter pressure vessel. 0.8 ml (0.016 millimole) of a fresh catalyst solution was added, and 251 g of N,N-diethylnerylamine was added. The second reaction was carried out, whereby citronellaldiethylenamine of the same purity as in the first reaction was obtained in nearly the same amount as in the first reaction.

Thereafter, the same procedure as above was repeated 12 times and the same results could be obtained.

Citronellaldiethylenamine thus obtained was hydrolyzed using sulfuric acid in the same manner as in Application Example 1 to obtain d-citronellal having a purity of 99.7%.

The optical rotation, $[\alpha]_D^{25}$, of the product was $+16.28°$, and in view of the literature value $[\alpha]_D = 16.5°$, the optical purity was 98.7%.

APPLICATION EXAMPLE 3

The air in an autoclave was replaced by nitrogen. Under a nitrogen atmosphere, 10 ml (0.133 millimole) of a tetrahydrofuran solution of the complex $[Rh(\pm)-p-Tolyl\ BINAP)_2]^+ClO_4^-$ prepared in Example 5, 360 ml of tetrahydrofuran and 181 g (0.8 moles) of 7-hydroxy-N,N-diethylgeranylamine were placed in the autoclave and reacted at 100° C. for 10 hours. After the reaction was completed, the reaction mixture was transferred into a distillation column. After the tetrahydrofuran was distilled away, the resulting residue was further distilled under reduced pressure at a temperature not exceeding 100° C. to obtain 180 g of the isomerized product, 7-hydroxycitronellaldiethylenamine (purity, 98.5%).

To the distillation residue was added 7 ml of n-heptane. The mixture was sufficiently stirred to dissolve high boiling components and by-product components in n-heptane and a n-heptane soluble portion was removed by filtration. 7 ml of fresh n-heptane was added and the same procedure as above was repeated. Thereafter, 360 ml of tetrahydrofuran was added to the distillation column and the remaining catalyst was dissolved therein to prepare a homogeneous solution. This homogeneous solution was returned to the autoclave. 0.71 ml (0.009 millimole) of a fresh catalyst solution was added, and 181 g of 7-hydroxy-N,N-diethylgeranylamine was added. The second reaction was carried out, whereby 7-hydroxycitronellaldiethylenamine having the same purity as in the first reaction was obtained in nearly the same amount as in the first reaction.

Thereafter, the same procedure as above was repeated 10 times and the same results could be obtained.

While the invention has been described in detail and with reference to specific embodiment thereof, it will be apparent to one skilled in the art that various changes and modifications can be made therein without departing from the spirit and scope thereof.

What is claimed is:

1. A rhodium-phosphine complex represented by the formula (I):

$$[Rh(p\text{-Tolyl BINAP})_2]^+ \ Y^- \qquad (I)$$

wherein p-Tolyl BINAP represents 2,2'-bis(di-p-tolylphosphino)-1,1'-binaphthyl which is a racemic substance or optically active substance; and Y represents $ClO_4$, $PF_6$, $BF_4$ or $PCl_6$.